United States Patent [19]

Jones

[11] Patent Number: 5,281,267
[45] Date of Patent: Jan. 25, 1994

[54] NO GROWTH BOTTOM PAINT OR COATING

[76] Inventor: Jack Jones, 6312 Fairfield Dr., Flourtown, Pa. 19031

[21] Appl. No.: 974,701

[22] Filed: Nov. 12, 1992

[51] Int. Cl.⁵ .............................................. C01B 16/02
[52] U.S. Cl. ................... 106/407; 106/415; 106/464; 252/175
[58] Field of Search ............... 114/67 R, 222; 106/15.05, 415, 464, 465, 407; 252/175, 80; 422/6

[56] References Cited

U.S. PATENT DOCUMENTS

| | | | |
|---|---|---|---|
| 117,462 | 7/1871 | Rickard | 252/180 |
| 324,236 | 8/1885 | Davis | 106/415 |
| 801,317 | 10/1905 | James | 106/415 |
| 1,234,264 | 7/1917 | Baumgardner | 106/415 |
| 1,276,861 | 8/1918 | Baumgardner | 106/415 |
| 1,302,252 | 4/1919 | Vuilleemet | 106/415 |
| 1,421,970 | 7/1922 | McCartney | 106/415 |
| 1,984,116 | 12/1934 | DeForest | 106/415 |
| 2,264,654 | 12/1941 | Boyd | 252/179 |
| 2,554,364 | 5/1951 | Hooten | 106/415 |
| 4,031,025 | 6/1977 | Vanlerberghe et al. | 252/180 |
| 4,167,597 | 9/1979 | Yoshida et al. | 114/67 R |
| 4,534,881 | 8/1985 | Sikes et al. | 252/180 |
| 4,585,560 | 4/1986 | Sikes et al. | 210/698 |
| 4,587,021 | 5/1986 | Wheeler et al. | 210/698 |
| 4,603,006 | 7/1986 | Sikes et al. | 252/180 |

Primary Examiner—Prince Willis, Jr.
Assistant Examiner—J. Silbermann
Attorney, Agent, or Firm—Hoffman, Wasson & Gitler

[57] ABSTRACT

A natural composition for preventing the growth of barnacles, grass, worms and the like on the hull of a boat or ship. The natural, powdered crustacean shell-based composition makes it easy to remove slime and scum formation and is safe to use on all boats or ships, including aluminum and steel. The natural composition incorporates pulverized, powdered, complete crustacean shells as the active ingredient, namely powdered mussel shells or the like.

4 Claims, No Drawings

NO GROWTH BOTTOM PAINT OR COATING

BACKGROUND OF THE INVENTION

This invention relates to a natural powdered composition for a paint or coating which prevents the growth of barnacles, grass, worms and the like on the hulls of boats or ships. The natural composition is safe to use on all boats, including, but not limited to, aluminum and steel. Further, this unique natural powdered composition is effective on boats kept in the water or in dry storage.

Anti-fouling compositions for coating the hulls of ships or boats are well known. These formulations utilized a number of chemically-based active ingredients and produced environmentally harmful results.

One solution was disclosed in U.S. Pat No. 117,462, issued on Jul. 25, 1871, which relates to the use of nitrogenized animal substances, acted upon chemically by mineral or other acids. Animal substances such as muscular fiber, gelatinized matter, such as hair, horn, skin or the like, were disclosed. These materials were not used in a submerged environment nor were they environmentally sound.

A second approach was suggested in U.S. Pat. Nos. 4,534,881; 4,585,560; 4,587,021 and 4,603,006 wherein complex methods and complex compounds for inhibiting the formation of $CaCO_3$ deposits on a surface were disclosed by applying a composition comprising an anti-calcification effective amount of a poly amino acid, a poly amino acid amide or derivative thereof. The fractions could be isolated from many $CaCO_3$-containing tissues, including molluscan shells, echinoderm skeletons, carbonate sands, crustacean exoskeletons, coral endoskeletons and the like through complex procedures wherein large portions of the items were discarded as waste.

The approach focused on using specific structural parts of the protein matrix from $CaCO_3$-forming animals and complex synthetic reproductions of these biopolymers.

Applicant has produced a novel, simplified formulation utilizing as its active ingredient a complete, natural, powdered crustacean shell, such as a mussel shell, clam shell, oyster shell or the like. The use of environmentally safe materials as the active ingredient in a no-growth paint or coating for the hulls of ships or boats was not heretofore contemplated by the references discussed above.

The non-toxic, pulverized, powdered complete crustacean shell active ingredient produced from discarded wastes is not only extremely desirable in its use as a non-growth paint or coating composition but also serves to protect the environment by using what was originally a waste product.

SUMMARY OF THE INVENTION

The present invention relates to a no-growth paint or coating formulation for preventing live growth on the hulls of boats or ships through use of a pulverized, powdered, complete, natural crustacean shell as its active ingredient.

The active, powdered, natural crustacean shell is combined with a filler, binder, opacifier, colorant and dissolved in a solvent to produce an environmentally safe and desirable paint or coating formulation.

A more complete appreciation of the invention, and many attendant advantages thereof, will be readily perceived as the same becomes better understood by reference to the following detailed description of the present invention.

DETAILED DESCRIPTION OF THE INVENTION

The present invention is based in the production of a natural, environmentally safe, non-toxic paint or coating formulation which prevents the growth of barnacles, grass, worms or the like on the hulls of ships or boats. The formulation is safe to use on all boats, including, but not limited to, aluminum and steel.

The formulation has as its active ingredient a pulverized, complete, natural crustacean shell powder. Crustaceans such as mussels, oysters, clams, crabs, coral or combinations thereof are all contemplated as the active ingredient with mussel shell powder being the preferred ingredient.

The active ingredient is combined with a filler, a binder, an opacifier, and a colorant. This resulting composition is then dissolved either in water or a vinyl-based solvent to produce the desired paint or coating.

In addition to the components discussed above, an anti-sag component and a defoamer can be added.

Additional enhancements can be made to supplement the base formulation without jeopardizing the overall effectiveness of the paint or coating.

Fillers such as talc, barytes or combinations thereof could be used in the resulting formulation. Any suitable binder can be utilized. Opacifiers such as titanium dioxide and any colorant would also be suitable.

The powdered components, active ingredient, filler, binder, opacifier and colorant are dissolved in a water-based solvent or a vinyl-based solvent which could include methyl isobutyl ketone and butyl acetate.

EXAMPLE 1

A preferred formulation of the non-growth paint or coating can be prepared in the following water-based solvent composition which produces 15 gallons of the formulation:

|  | Wt (lbs) |
| --- | --- |
| MUSSEL SHELL POWDER | 40 |
| BINDER | 53 |
| FILLER | 21 |
| OPACIFIER | 6 |
| COLORANT | 1.5 |

Water is included to complete the formulation and a dispersant, defoamer, thickener, or any desired material can be incorporated in amounts, as desired.

When applied to the hull of a boat or ship, superior non-growth properties are obtained.

EXAMPLE 2

A preferred formulation of the non-growth paint or coating can be prepared in the following vinyl-based solvent composition which produces 6 ½ gallons of the formulation:

|  | Wt (lbs) |
| --- | --- |
| MUSSEL SHELL POWDER | 23.5 |
| BINDER | 12.5 |
| FILLER | 11.0 |
| OPACIFIER | 4.5 |

| -continued | |
| --- | --- |
| | Wt (lbs) |
| COLORANT | 2.5 |

A solvent including methyl isobutyl ketone and butyl acetate is added to complete the formulation. A dispersant, defoamer, anti-sag material, thickener, or any desired material can be incorporated in amounts, as desired.

Two coats of the formulation were applied by brush to 16 test panels as well as to the hulls of boats or ships for periods exceeding 18 months with no surface growth resulting.

The superior results obtained through test use of the formulation have no where been equalled.

The formulations can be applied by brush, or any coating technique available.

The examples discussed above are for reference purposes and do not limit the scope of the invention.

The present formulations are useful for the prevention of calcified formations by organisms such as barnacles, mollusks, sea urchins, and calcareous algae, among others. The formulation uniquely interferes with the metabolism of the organism, thereby inhibiting calcification.

The invention now being fully described, it will be apparent to one of ordinary skill in the art that many changes and modifications can be made thereto, without departing from the spirit or scope of the invention as set forth herein.

What is claimed is:

1. A natural formulation for preventing live growth on the hulls of boats or ships comprising as an active ingredient pulverized mussel shell powder derived from complete mussel shells and a titanium dioxide opacifier.

2. A natural formulation in accordance with claim 1, a filler selected from the group consisting of talc, barytes and combinations thereof.

3. A natural formulation in accordance with claim 2, said formulation is dissolved in a water-based solvent or a solvent selected from the group consisting of methyl isobutyl ketone and butyl acetate.

4. A natural formulation for preventing live growth on the hulls of boars or ships comprising:
   a) as an active ingredient, pulverized mussel shell powder derived from complete mussel shells;
   b) a titanium dioxide opacifier;
   c) a filler selected from talc, barytes or combinations thereof; and
   d) a solvent which is water, methyl isobutyl ketone or butyl acetate.

* * * * *